US011166759B2

(12) United States Patent
Kappus et al.

(10) Patent No.: US 11,166,759 B2
(45) Date of Patent: Nov. 9, 2021

(54) SURGICAL FORCEPS

(71) Applicant: COVIDIEN LP, Mansfield, MA (US)

(72) Inventors: John J. Kappus, Denver, CO (US);
David N. Heard, Boulder, CO (US);
Joe D. Sartor, Longmont, CO (US)

(73) Assignee: Covidien LP, Mansfield, MA (US)

( * ) Notice: Subject to any disclaimer, the term of this patent is extended or adjusted under 35 U.S.C. 154(b) by 833 days.

(21) Appl. No.: 15/944,115

(22) Filed: Apr. 3, 2018

(65) Prior Publication Data
US 2018/0333197 A1 Nov. 22, 2018

Related U.S. Application Data

(60) Provisional application No. 62/506,653, filed on May 16, 2017.

(51) Int. Cl.
A61B 18/14 (2006.01)
A61B 17/285 (2006.01)
(Continued)

(52) U.S. Cl.
CPC ........ *A61B 18/1445* (2013.01); *A61B 17/282* (2013.01); *A61B 17/285* (2013.01);
(Continued)

(58) Field of Classification Search
CPC ............ A61B 18/1442; A61B 18/1445; A61B 18/1447; A61B 2018/1442;
(Continued)

(56) References Cited

U.S. PATENT DOCUMENTS 371,664 A 10/1887 Brannan et al.
702,472 A 6/1902 Pignolet
(Continued)

FOREIGN PATENT DOCUMENTS

CA 2104423 A1 2/1994
DE 2415263 A1 10/1975
(Continued)

OTHER PUBLICATIONS

Annotated_Guerra_Figure_5 (Year: 2021).*
Extended European Search Report issued in corresponding European Application No. 18172276.0 dated Jul. 19, 2018, 8 pages.

*Primary Examiner* — Linda C Dvorak
*Assistant Examiner* — Nicholas S Borsch
(74) *Attorney, Agent, or Firm* — Carter, DeLuca & Farrell LLP

(57) ABSTRACT

A surgical forceps including an end effector assembly has first and second jaw members. At least one of the first or second jaw members has a jaw frame defining a channel therein, an insulative member disposed within the channel of the jaw frame, and an electrically-conductive plate having a tissue contacting surface and at least one folded side portion. The insulative member includes a top portion having a tissue facing surface. The tissue contacting surface of the electrically-conductive plate is disposed on the tissue facing surface of the insulative member. The at least one folded side portion of the electrically-conductive plate is folded over the top portion of the insulative member such that the electrically-conductive plate conforms to a shape of the top portion of the insulative member.

17 Claims, 8 Drawing Sheets

(51) Int. Cl.
*A61B 17/28* (2006.01)
*A61B 18/00* (2006.01)

(52) U.S. Cl.
CPC ...... *A61B 17/2841* (2013.01); *A61B 18/1482* (2013.01); *A61B 2018/0063* (2013.01); *A61B 2018/00083* (2013.01); *A61B 2018/00589* (2013.01); *A61B 2018/00595* (2013.01); *A61B 2018/00607* (2013.01); *A61B 2018/1405* (2013.01); *A61B 2018/1452* (2013.01); *A61B 2018/1497* (2013.01)

(58) Field of Classification Search
CPC ...... A61B 2018/145; A61B 2018/1455; A61B 2018/146; A61B 2018/1462; A61B 2017/2808; A61B 17/2812; A61B 17/2816; A61B 2017/2825; A61B 2017/2829; A61B 17/2833; A61B 2017/2837; A61B 2017/2845; A61B 17/29; A61B 2017/2901; A61B 2017/2902; A61B 2017/2903; A61B 2017/2904; A61B 2017/2905; A61B 2017/2906; A61B 2017/2908; A61B 17/2909; A61B 2017/291; A61B 2017/2911; A61B 2017/2912; A61B 2017/2913; A61B 2017/2915; A61B 2017/2916; A61B 2017/2917; A61B 2017/2918; A61B 2017/2919; A61B 2017/292; A61B 2017/2922; A61B 2017/2923; A61B 2017/2924; A61B 2017/2925; A61B 2017/2926; A61B 2017/2927; A61B 2017/2929; A61B 2017/293; A61B 2017/2931; A61B 2017/2933; A61B 2017/2934; A61B 2017/2936; A61B 2017/2937; A61B 2017/2938; A61B 2017/2939; A61B 2017/294; A61B 2017/2941; A61B 2017/2943; A61B 2017/2944; A61B 2017/2945; A61B 2017/2946; A61B 2017/2947; A61B 2017/2948; A61B 17/295; A61B 17/30; A61B 2017/301; A61B 2017/303; A61B 2017/305; A61B 2017/306; A61B 2017/308; A61B 2018/00071; A61B 2018/00077; A61B 2018/00083; A61B 17/28; A61B 2017/2932; A61B 2018/0016; A61B 2018/00208; A61B 17/282; A61B 17/285; A61B 17/2841; A61B 18/1482; A61B 2018/00589; A61B 2018/00607; A61B 2018/0063; A61B 2018/1405; A61B 2018/1452; A61B 2018/1497

See application file for complete search history.

(56) References Cited

U.S. PATENT DOCUMENTS

| | | |
|---|---|---|
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,279,753 A | 4/1942 | Knopp |
| 2,305,156 A | 12/1942 | Grubel |
| 2,327,353 A | 8/1943 | Karle |
| 2,632,661 A | 3/1953 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,913,586 A | 10/1975 | Baumgarten |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Koch et al. |
| 4,715,122 A | 12/1987 | Linden |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |

(56) References Cited

U.S. PATENT DOCUMENTS

| | | |
|---|---|---|
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Heidmueller et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,823 A | 10/1995 | Richardson et al. |
| 5,454,827 A | 10/1995 | Aust et al. |
| 5,456,140 A | 10/1995 | Linden et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,478,351 A | 12/1995 | Meade et al. |
| 5,480,406 A | 1/1996 | Nolan et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsuruta et al. |
| 5,582,617 A | 12/1996 | Klieman et al. |
| 5,585,896 A | 12/1996 | Yamazaki et al. |

(56) References Cited

U.S. PATENT DOCUMENTS

| | | |
|---|---|---|
| 5,590,570 A | 1/1997 | LeMaire, III et al. |
| 5,591,181 A | 1/1997 | Stone et al. |
| 5,591,202 A | 1/1997 | Slater et al. |
| 5,597,107 A | 1/1997 | Knodel et al. |
| 5,599,350 A | 2/1997 | Schulze et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,611,798 A | 3/1997 | Eggers |
| 5,611,808 A | 3/1997 | Hossain et al. |
| 5,611,813 A | 3/1997 | Lichtman |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,674,229 A | 10/1997 | Tovey et al. |
| 5,681,282 A | 10/1997 | Eggers et al. |
| 5,688,270 A | 11/1997 | Yates et al. |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,646 A | 7/1998 | Koblish et al. |
| 5,779,701 A | 7/1998 | McBrayer et al. |
| H1745 H | 8/1998 | Paraschac |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,093 A | 10/1998 | Williamson, IV et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,859,527 A | 1/1999 | Cook |
| 5,860,976 A | 1/1999 | Billings et al. |
| 5,876,401 A | 3/1999 | Schulze et al. |
| 5,876,412 A | 3/1999 | Piraka |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,941,869 A | 8/1999 | Patterson et al. |
| 5,944,718 A | 8/1999 | Austin et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka |
| 6,017,358 A | 1/2000 | Yoon et al. |
| 6,021,693 A | 2/2000 | Feng-Sing |
| 6,024,741 A | 2/2000 | Williamson, IV et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |

(56) References Cited

U.S. PATENT DOCUMENTS

| | | |
|---|---|---|
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,060,695 A | 5/2000 | Harle et al. |
| 6,066,139 A | 5/2000 | Ryan et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,096,031 A | 8/2000 | Mitchell et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 | 1/2001 | Wrublewski et al. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | Van De Moer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan, Jr. |
| 6,302,424 B1 | 10/2001 | Gisinger et al. |
| 6,312,430 B1 | 11/2001 | Wilson et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,503,248 B1 | 1/2003 | Levine |
| 6,506,189 B1 | 1/2003 | Rittman, III et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,251 B1 | 2/2003 | Ni et al. |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,544,264 B2 | 4/2003 | Levine et al. |
| 6,545,239 B2 | 4/2003 | Spedale et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,569,162 B2 | 5/2003 | He |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | de Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |

(56) References Cited

U.S. PATENT DOCUMENTS

| | | |
|---|---|---|
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2 | 3/2005 | Treat et al. |
| 6,887,240 B1 | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kidooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al. |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podhajsky et al. |
| 7,246,734 B2 | 7/2007 | Shelton, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald |
| 7,344,268 B2 | 3/2008 | Jigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |

(56) References Cited

U.S. PATENT DOCUMENTS

| | | |
|---|---|---|
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 7,922,953 B2 | 4/2011 | Guerra |
| 8,333,765 B2 | 12/2012 | Johnson et al. |
| 8,623,018 B2 * | 1/2014 | Horner ............... A61B 18/1442 606/51 |
| 9,510,906 B2 | 12/2016 | Boudreaux et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078577 A1 | 4/2003 | Truckai et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0148035 A1 | 7/2004 | Barrett et al. |
| 2004/0162557 A1 | 8/2004 | Tetzlaff et al. |
| 2004/0193153 A1 | 9/2004 | Sartor et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0225288 A1 | 11/2004 | Buysse et al. |
| 2004/0230189 A1 | 11/2004 | Keppel |
| 2004/0236325 A1 | 11/2004 | Tetzlaff et al. |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter et al. |
| 2005/0004564 A1 | 1/2005 | Wham et al. |
| 2005/0004568 A1 | 1/2005 | Lawes et al. |
| 2005/0004569 A1 | 1/2005 | Witt et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113828 A1 | 5/2005 | Shields et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 * | 4/2007 | Guerra ............... A61B 18/1445 156/242 |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 * | 5/2007 | Dumbauld ............ A61B 18/085 606/51 |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |

(56) References Cited

U.S. PATENT DOCUMENTS

| | | |
|---|---|---|
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015567 A1 | 1/2008 | Kimura |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0187188 A1 | 7/2009 | Guerra et al. |
| 2011/0071523 A1 | 3/2011 | Dickhans |
| 2016/0199122 A1* | 7/2016 | Jones ............... A61B 18/1442 606/52 |

FOREIGN PATENT DOCUMENTS

| | | |
|---|---|---|
| DE | 02514501 A1 | 10/1976 |
| DE | 2627679 A1 | 1/1977 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 29616210 U1 | 11/1996 |
| DE | 19608716 C1 | 4/1997 |
| DE | 19751106 A1 | 5/1998 |
| DE | 19738457 B4 | 3/1999 |
| DE | 19751108 A1 | 5/1999 |
| DE | 19828976 A1 | 2/2000 |
| DE | 20001204 U1 | 3/2000 |
| EP | 0467501 A1 | 1/1992 |
| EP | 0541930 A1 | 5/1993 |
| EP | 0572131 A1 | 12/1993 |
| EP | 0584787 A1 | 3/1994 |
| EP | 0589555 A1 | 3/1994 |
| EP | 0589453 A3 | 4/1994 |
| EP | 0624348 A3 | 6/1995 |
| EP | 0364216 B1 | 1/1996 |
| EP | 0518230 B1 | 5/1996 |
| EP | 0517243 B1 | 9/1997 |
| EP | 0878169 A1 | 11/1998 |
| EP | 0623316 B1 | 3/1999 |
| EP | 0650701 B1 | 3/1999 |
| EP | 0923907 A1 | 6/1999 |
| EP | 0986990 A1 | 3/2000 |
| EP | 1034747 A1 | 9/2000 |
| EP | 1034748 | 9/2000 |
| EP | 0694290 B1 | 11/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1082944 | 3/2001 |
| EP | 1177771 | 2/2002 |
| EP | 1159926 A3 | 3/2003 |
| EP | 0717966 B1 | 4/2003 |
| EP | 1301135 | 4/2003 |
| EP | 0887046 B1 | 7/2003 |
| EP | 1330991 A1 | 7/2003 |
| EP | 1486177 | 6/2004 |
| EP | 1472984 | 11/2004 |
| EP | 0754437 B2 | 12/2004 |
| EP | 1025807 B1 | 12/2004 |
| EP | 0774232 B1 | 1/2005 |
| EP | 0853922 B1 | 2/2005 |
| EP | 1527747 | 5/2005 |
| EP | 1530952 | 5/2005 |
| EP | 1532932 A1 | 5/2005 |
| EP | 1535581 | 6/2005 |
| EP | 1609430 A1 | 12/2005 |
| EP | 1034746 B1 | 3/2006 |
| EP | 1632192 | 3/2006 |
| EP | 1642543 | 4/2006 |
| EP | 1645238 A1 | 4/2006 |
| EP | 1645240 A2 | 4/2006 |
| EP | 1649821 | 4/2006 |
| EP | 0875209 B1 | 5/2006 |
| EP | 1707143 A1 | 10/2006 |
| EP | 1769765 A1 | 4/2007 |
| EP | 1769766 | 4/2007 |
| EP | 1929970 | 6/2008 |
| EP | 1683496 | 12/2008 |
| EP | 2926754 A2 | 10/2015 |
| GB | 221341 A | 9/1924 |
| GB | 221443 A | 9/1924 |
| GB | 623316 | 5/1949 |
| GB | 1490585 | 11/1977 |
| GB | 2213416 A | 8/1989 |
| GB | 2214430 A | 9/1989 |
| JP | 61501068 | 9/1984 |
| JP | 6502328 | 3/1992 |
| JP | 55106 | 1/1993 |
| JP | 0540112 | 2/1993 |
| JP | 06343644 A | 12/1994 |
| JP | 07265328 A | 10/1995 |
| JP | H0856955 | 5/1996 |
| JP | 08252263 A | 10/1996 |
| JP | H0910223 A | 1/1997 |
| JP | 11244298 A | 9/1999 |
| JP | 2000252831 A | 9/2000 |
| JP | 2000289472 A | 10/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |

(56) References Cited

FOREIGN PATENT DOCUMENTS

| | | | |
|---|---|---|---|
| SU | 401367 | A1 | 10/1973 |
| WO | 8900757 | | 1/1989 |
| WO | 9204873 | | 4/1992 |
| WO | 9206642 | | 4/1992 |
| WO | 9321845 | | 11/1993 |
| WO | 9408524 | | 4/1994 |
| WO | 9420025 | | 9/1994 |
| WO | 9502369 | | 1/1995 |
| WO | 9507662 | | 3/1995 |
| WO | 9515124 | | 6/1995 |
| WO | 9605776 | | 2/1996 |
| WO | 9622056 | A1 | 7/1996 |
| WO | 9613218 | | 9/1996 |
| WO | 9700646 | | 1/1997 |
| WO | 9700647 | | 1/1997 |
| WO | 9710764 | | 3/1997 |
| WO | 9724073 | | 7/1997 |
| WO | 9724993 | | 7/1997 |
| WO | 9827880 | | 7/1998 |
| WO | 9903407 | | 1/1999 |
| WO | 9903408 | | 1/1999 |
| WO | 9903409 | | 1/1999 |
| WO | 9912488 | | 3/1999 |
| WO | 9923933 | A2 | 5/1999 |
| WO | 9940857 | | 8/1999 |
| WO | 9940861 | | 8/1999 |
| WO | 9951158 | | 10/1999 |
| WO | 9966850 | | 12/1999 |
| WO | 0024330 | | 5/2000 |
| WO | 0024331 | | 5/2000 |
| WO | 0036986 | A1 | 6/2000 |
| WO | 0041638 | | 7/2000 |
| WO | 0047124 | | 8/2000 |
| WO | 0053112 | | 9/2000 |
| WO | 0117448 | | 3/2001 |
| WO | 0154604 | A1 | 8/2001 |
| WO | 0166026 | A2 | 9/2001 |
| WO | 02/07627 | | 1/2002 |
| WO | 02067798 | | 9/2002 |
| WO | 02080783 | | 10/2002 |
| WO | 02080784 | | 10/2002 |
| WO | 02080785 | | 10/2002 |
| WO | 02080786 | | 10/2002 |
| WO | 02080793 | A1 | 10/2002 |
| WO | 02080794 | | 10/2002 |
| WO | 02080795 | | 10/2002 |
| WO | 02080796 | A1 | 10/2002 |
| WO | 02080797 | | 10/2002 |
| WO | 02080798 | | 10/2002 |
| WO | 02080799 | | 10/2002 |
| WO | 02081170 | | 10/2002 |
| WO | 02098313 | A1 | 12/2002 |
| WO | 03061500 | | 7/2003 |
| WO | 03101311 | | 12/2003 |
| WO | 03090630 | A3 | 4/2004 |
| WO | 2004032776 | A1 | 4/2004 |
| WO | 2004032777 | A1 | 4/2004 |
| WO | 2004052221 | A1 | 6/2004 |
| WO | 2004/073753 | A2 | 9/2004 |
| WO | 2004073488 | A2 | 9/2004 |
| WO | 2004073490 | A2 | 9/2004 |
| WO | 2004082495 | A1 | 9/2004 |
| WO | 2004098383 | A2 | 11/2004 |
| WO | 2004103156 | | 12/2004 |
| WO | 2005004734 | A1 | 1/2005 |
| WO | 2005004735 | A1 | 1/2005 |
| WO | 2005110264 | A3 | 4/2006 |
| WO | 2008/045348 | A2 | 4/2008 |
| WO | 2008045350 | A2 | 4/2008 |

\* cited by examiner

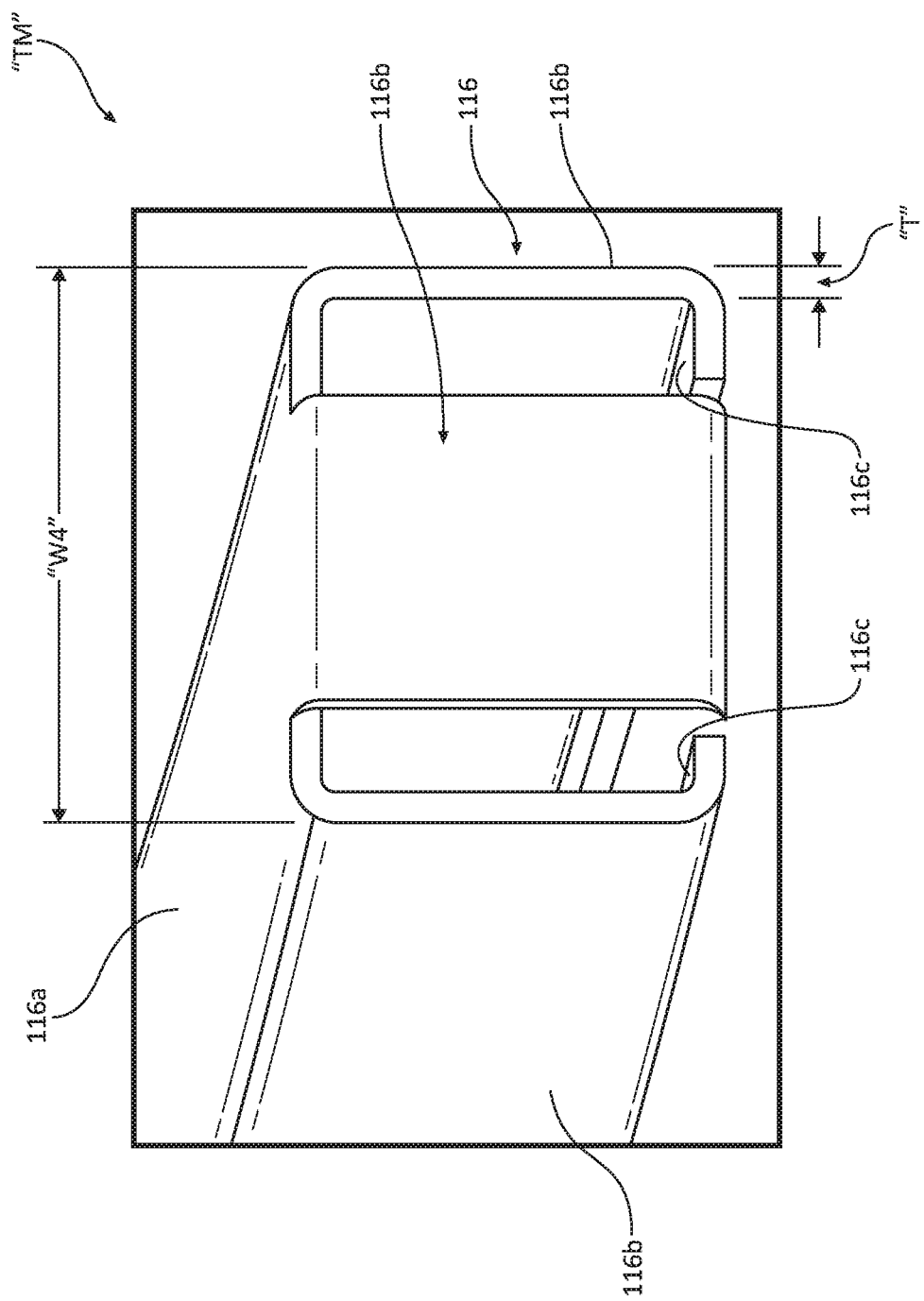

SURGICAL FORCEPS

CROSS REFERENCE TO RELATED APPLICATION

The present application claims the benefit of and priority to U.S. Provisional Application Ser. No. 62/506,653, filed on May 16, 2017 the entire contents of which are incorporated herein by reference.

BACKGROUND

Technical Field

The present disclosure relates to surgical instruments and, more particularly, to a surgical forceps configured for treating and/or cutting tissue.

Background of Related Art

A surgical forceps is a plier-like device which relies on mechanical action between its jaws to grasp, clamp, and constrict tissue. Energy-based surgical forceps utilize both mechanical clamping action and energy to affect hemostasis by heating tissue to treat, e.g., coagulate, cauterize, and/or seal, tissue. However, as a by-product of treating a target area of tissue, thermal spread may result in inadvertent treating of tissue outside of the target area. It is therefore advantageous to treat tissue in as small a target area as possible, without compromising the effectiveness of the treatment, and to inhibit heating of tissue outside of the target area. Additionally, retained jaw heat can be sufficient to damage tissue if the jaw is allowed to touch unintended tissue before it sufficiently cools down. This retained heat can make it necessary for the surgeon to pause to allow the jaws to cool before continuing with additional treatments to other target tissue. Accordingly, a need exists for a device with both a very narrow sealing zone and very low thermal mass to minimize these issues without compromising functionality.

SUMMARY

As used herein, the term "distal" refers to the portion that is being described which is closer to a patient, while the term "proximal" refers to the portion that is being described which is further from a patient. Further, to the extent consistent, any of the aspects described herein may be used in conjunction with any or all of the other aspects described herein.

In accordance with the present disclosure, a surgical forceps including an end effector assembly is provided. The end effector assembly includes first and second jaw members. At least one of the first or second jaw members is movable relative to the other between a first position and a second position. At least one of the first or second jaw members has a jaw frame defining a channel therein, an insulative member disposed within the channel of the jaw frame, and an electrically-conductive plate having a tissue contacting surface and at least one folded side portion. The insulative member includes a top portion having a tissue facing surface. The tissue contacting surface of the electrically-conductive plate is disposed on the tissue facing surface of the insulative member. The at least one folded side portion of the electrically-conductive plate is folded over the top portion of the insulative member such that the electrically-conductive plate conforms to a shape of the top portion of the insulative member.

In aspects, the insulative member further includes a base portion and a body portion extending between the top portion and the base portion, wherein at least one longitudinal groove is formed between the top portion and the base portion.

In aspects, the at least one folded side portion of the electrically-conductive plate includes a bottom edge disposed within the at least one longitudinal groove of the insulative member.

In aspects, the end effector assembly further includes an outer insulative housing formed about the jaw frame and having an opening extending therethrough, wherein at least a portion of the tissue contacting surface of the electrically-conductive plate is accessible through the opening of the outer insulative housing.

In aspects, the outer insulative housing defines a tissue contacting surface, the tissue contacting surface of the outer insulative housing being raised above the tissue contacting surface of the electrically-conductive plate.

In aspects, the top portion of the insulative member defines a first width and the base portion of the insulative member defines a second width greater than the first width.

In aspects, the tissue contacting surface of the electrically-conductive plate defines a fourth width which is between about 0.020 inches and about 0.080 inches.

In aspects, the electrically-conductive plate defines a thickness of about 0.001 inches to about 0.004 inches.

In accordance with another aspect of the present disclosure, a surgical forceps including an end effector assembly is provided. The end effector assembly includes first and second jaw members. At least one of the first or second jaw members is movable relative to the other between a first position and second position. At least one of the first or second jaw members has a jaw frame defining a channel therein, an insulative member disposed within the channel of the jaw frame, an electrically-conductive plate having a tissue contacting surface and at least one folded side portion, and an outer insulative housing enclosing the jaw frame. The insulative member includes a top portion, a base portion coupled to the top portion, and at least one longitudinal groove defined therebetween. The electrically-conductive plate is disposed on the top portion of the insulative member and folded about the insulative member such that the at least one folded side portion is folded into the at least one longitudinal groove. The outer insulative housing includes a tissue contacting surface defining an opening. At least a portion of the electrically-conductive plate is accessible through the opening of the outer insulative housing to treat tissue.

In aspects, the tissue contacting surface of the electrically-conductive plate is recessed relative to the tissue contacting surface of the outer insulative housing.

In aspects, the tissue contacting surface of the electrically-conductive plate includes a first area and the tissue contacting surface of the outer insulative housing includes a second area, the first and second areas within an order of magnitude relative to one another.

In aspects, the at least one folded side portion of the electrically-conductive plate includes a bottom edge, wherein the bottom edge is folded within the at least one longitudinal groove of the insulative member.

In aspects, the insulative member further includes a body portion extending between the top portion and the base portion, wherein the body portion defines a third width less than the first width of the top portion and the second width of the base portion, such that the at least one longitudinal groove is formed between the top portion and the base portion.

In accordance with another aspect of the present disclosure, a surgical forceps including a housing, a shaft, an end effector assembly, and a drive assembly is provided. The shaft is supported by the housing and includes a distal end portion and a proximal end portion. The end effector assembly includes first and second jaw members. At least one of the first or second jaw members is movable relative to the other between a first position and a second position. At least one of the first or second jaw members has a jaw frame defining a channel therein, an insulative member disposed within the channel of the jaw frame, and an electrically-conductive plate having a tissue contacting surface and at least one folded side portion. The insulative member includes a top portion having a tissue facing surface. The tissue contacting surface of the electrically-conductive plate is disposed on the tissue facing surface of the insulative member. The at least one folded side portion of the electrically-conductive plate is folded over the top portion of the insulative member such that the electrically-conductive plate conforms to a shape of the top portion of the insulative member. The drive assembly is disposed within the housing and is configured to impart movement of the at least one of the first or second jaw members between the first and second positions.

BRIEF DESCRIPTION OF THE DRAWINGS

Various aspects and features of the present disclosure are described herein with reference to the drawings wherein:

FIG. 5 is a front, perspective view of the area of detail in FIG. 4B referenced as "5," with the insulative member removed.

DETAILED DESCRIPTION

The present disclosure is directed to a surgical forceps including an end effector having jaws that are configured to minimize the heat affected zone surrounding a target tissue. In embodiments, the heat affected zone may be minimized by reducing the thermal mass of a conductive element, such as, for example, an electrically conductive seal plate of the jaws by reducing the overall width and thickness thereof. It is contemplated that the smaller footprint of the electrically conductive seal plate disclosed herein may yield faster heating and cooling of the electrically conductive seal plate, thereby resulting in an overall reduction in treatment cycle time.

Figure 1:
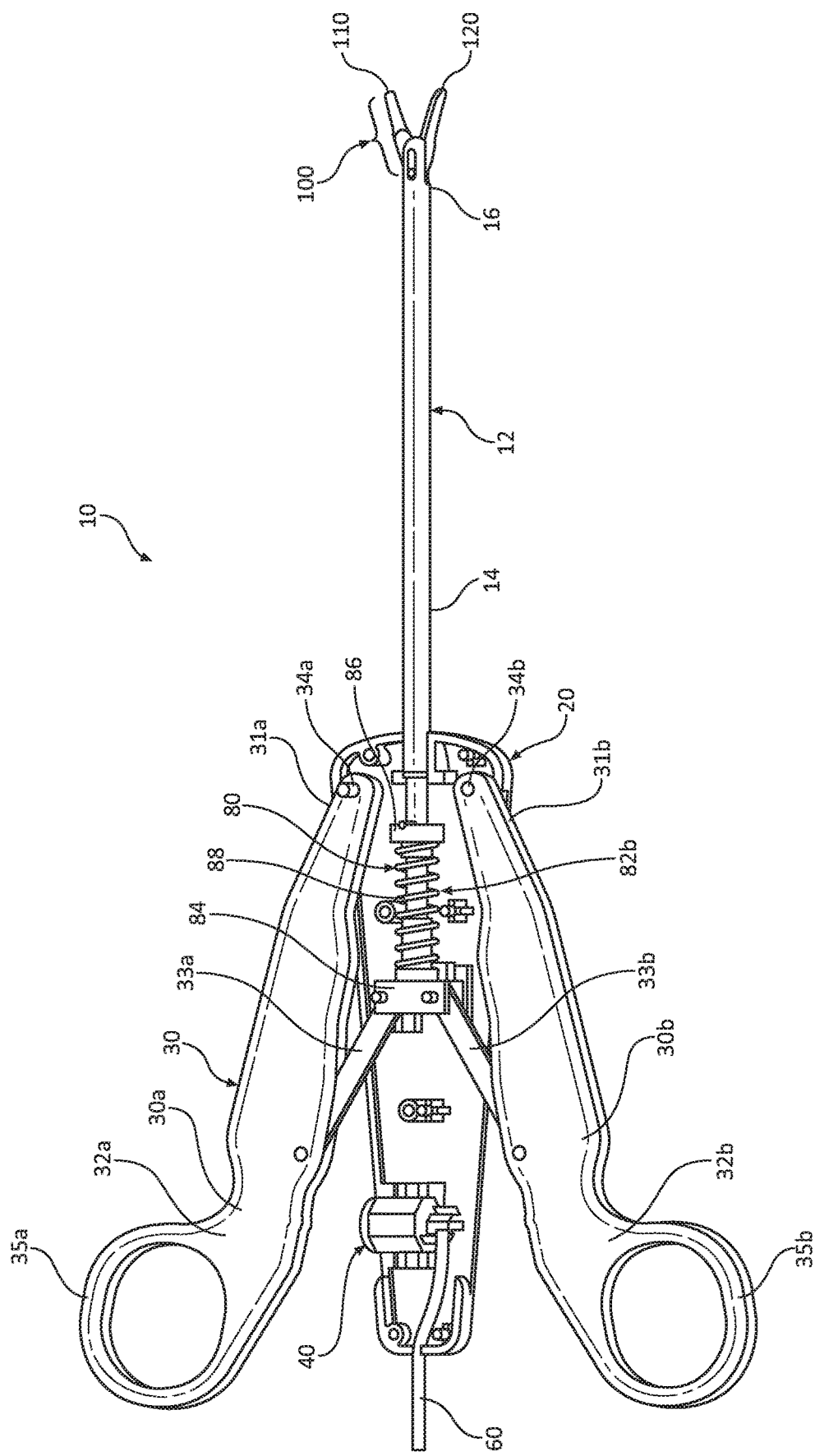
FIG. 1 is a top view of a surgical forceps provided in accordance with the present disclosure, wherein a portion of the housing is removed and the end effector assembly is shown in an open configuration.

With reference to FIG. 1, a surgical forceps configured for use in accordance with the present disclosure is shown generally identified by reference numeral 10. Forceps 10 is configured for use in various surgical procedures and generally includes a housing 20, a handle assembly 30, an activation assembly 40, and an end effector assembly 100 which mutually cooperate to grasp and treat tissue. Forceps 10 further includes a shaft 12 having a proximal end portion 14 that mechanically engages housing 20 and a distal end portion 16 that mechanically engages end effector assembly 100. A cable 60 is adapted to connect forceps 10 to a source of energy, e.g., a generator (not shown), although forceps 10 may alternatively be configured as a battery powered instrument.

Handle assembly 30 includes two movable handles 30a and 30b disposed on opposite sides of housing 20. Handles 30a and 30b are movable relative to one another to actuate end effector assembly 100, as will be described in greater detail below.

Continuing with reference to FIG. 1, end effector assembly 100 is attached at distal end portion 16 of shaft 12 and includes opposing first and second jaw members 110, 120. Handles 30a and 30b of handle assembly 30 ultimately connect to a drive assembly 80 disposed within housing 20 and extending through shaft 12 which, together, cooperate to impart movement of jaw members 110 and 120 from an open position wherein jaw members 110 and 120 are disposed in spaced relation relative to one another, to a closed position wherein jaw members 110 and 120 cooperate to grasp tissue therebetween, in response to movement of handles 30a, 30b from an un-actuated position, wherein handles 30a, 30b are spaced-apart from housing 20, and an actuated position, wherein handles 30a, 30b are approximated relative to housing 20.

Figure 2A:
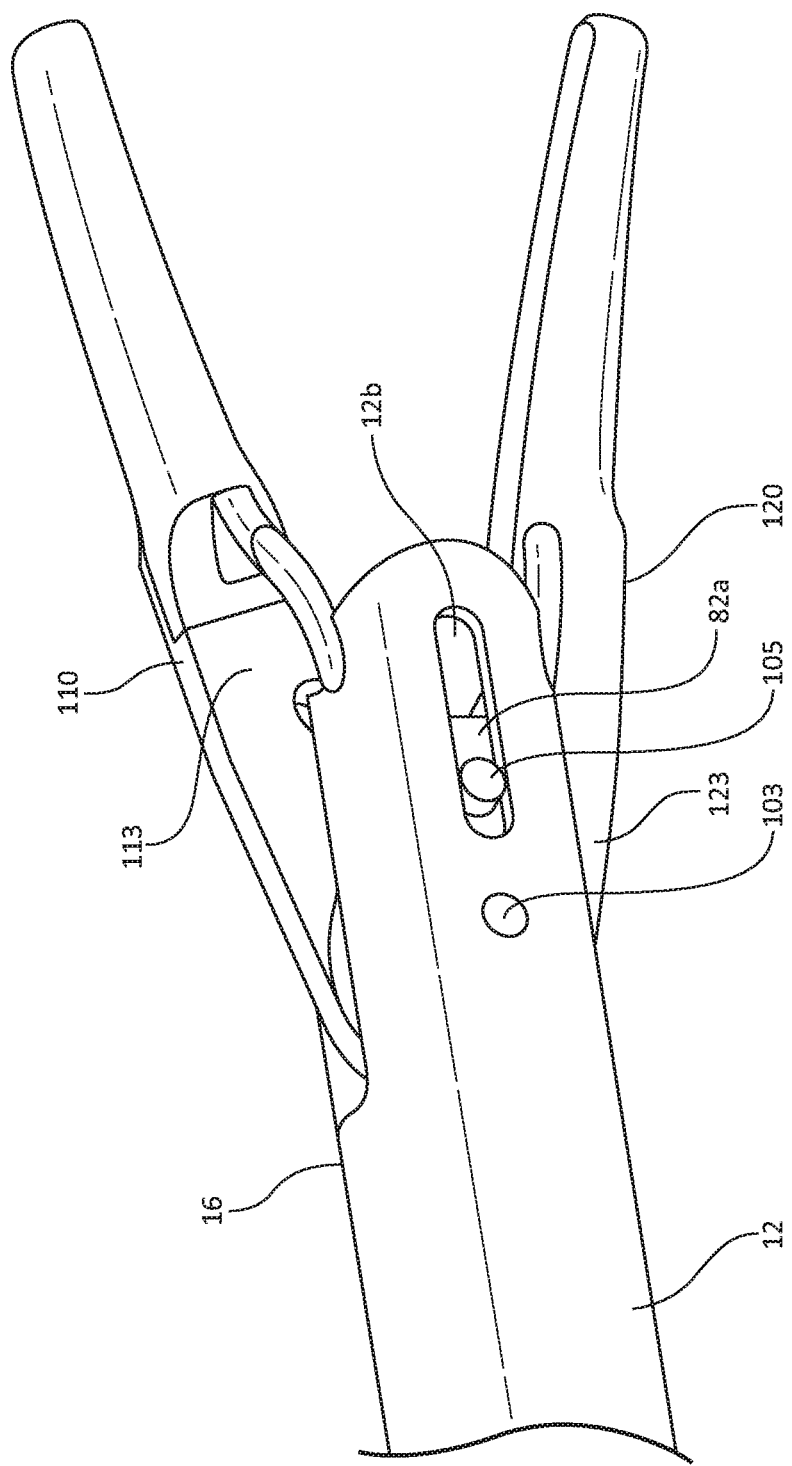
FIG. 2A is a side, perspective view of the distal portion of the surgical forceps of FIG. 1, wherein the end effector assembly is shown in the open configuration.
Figure 2B:
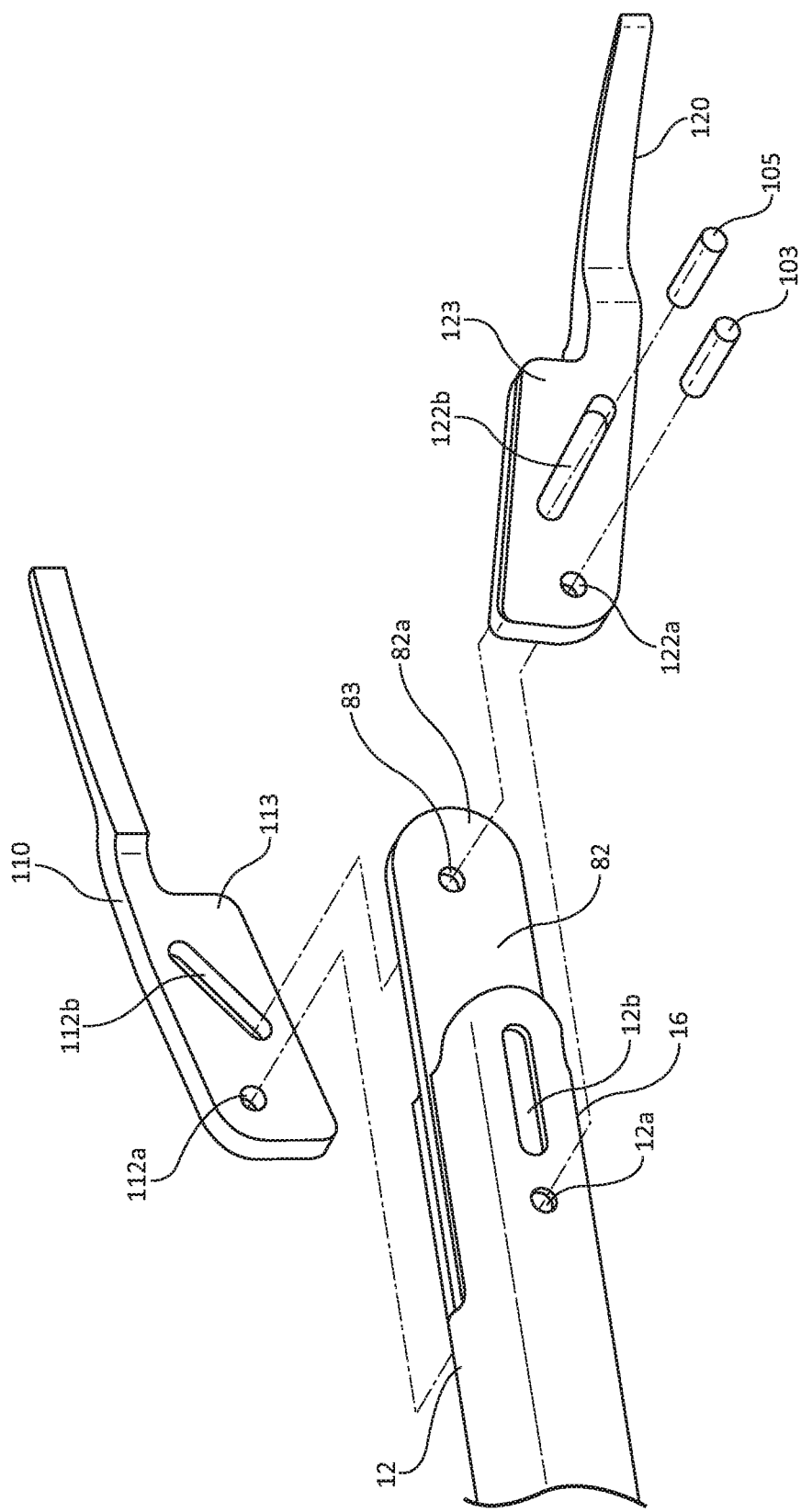
FIG. 2B is a side view of the distal portion of the surgical forceps of FIG. 1, shown with parts separated.

With particular reference to FIGS. 2A and 2B, in conjunction with FIG. 1, first and second jaw members 110, 120 each include a proximal flange 113, 123. Proximal flanges 113, 123 of jaw members 110, 120 are pivotably coupled to one another and shaft 12 via a pivot pin 103. Specifically, pivot pin 103 extends through respective pivot apertures 112a, 122a of proximal flanges 113, 123 and a pivot aperture 12a of shaft 12 to pivotably couple jaw members 110, 120 to one another and shaft 12. End effector assembly 100 is designed as a bilateral assembly, e.g., where both jaw member 110 and jaw member 120 are moveable about pivot 103 relative to one another and to shaft 12. However, end effector assembly 100 may alternatively be configured as a unilateral assembly, e.g., where one of the jaw members 110, 120 is fixed relative to shaft 12 and the other jaw member 110, 120 is moveable about pivot 103 relative to shaft 12 and the fixed jaw member 110, 120.

Proximal flanges 113, 123 of jaw members 110, 120, respectively, each further include an oppositely-angled cam slot 112b, 122b defined therethrough that is configured to receive a drive pin 105. Drive pin 105 also extends through an aperture 83 at a distal end portion 82a of a drive bar 82 of drive assembly 80, such that, as will be described in greater detail below, reciprocation of drive bar 82 through shaft 12 effects pivoting of jaw members 110, 120 relative to one another between the open and closed positions. A longitudinally-extending slot 12b defined through shaft 12 on either side thereof is configured to receive the ends of drive bar 105 to confine drive pin 105 to longitudinal translation therethrough.

Drive assembly 80, as noted above, includes drive bar 82. Drive assembly 80 also includes a drive block 84 disposed within housing 20 and slidably disposed about a proximal end portion 82b of drive bar 82, a drive collar 86 engaged about proximal end portion 82b of drive bar 82, and a spring 88 disposed about proximal end portion 82b of drive bar 82 and positioned between drive block 84 and drive collar 86. Drive block 84 is coupled to handles 30a, 30b via link arms 33a, 33b, respectively. Handles 30a and 30b are pivotably coupled to housing 20 at their respective distal end portions 31a, 31b via pivot pins 34a, 34b, respectively, and extend proximally to proximal end portions 32a, 32b, respectively, thereof. Finger rings 35a, 35b are defined at the respective proximal end portions 32a, 32b of handles 30a, 30b.

Handles 30a, 30b are coupled to drive block 84 such that pivoting of handles 30a, 30b about pivot pins 34a, 34b, respectively, from the un-actuated position to the actuated position translates drive block 84 distally through housing 20. Initially, this distal translation of drive block 84 urges spring 88 distally to, in turn, urge drive collar 86 distally. Since drive collar 86 is engaged about drive bar 82, distal urging of drive collar 86 translates drive bar 82 distally through shaft 12 to effect pivoting of jaw members 110, 120 from the open position towards the closed position. When sufficient force inhibiting further approximation of jaw members 110, 120, e.g., the force of tissue grasped therebetween resisting further compression, is imparted to drive bar 82, further pivoting of handles 30a, 30b translates drive block 84 distally through housing 20 to compress spring 88 such that drive collar 86 and drive bar 82 are maintained in position. In this manner, drive assembly 80 defines a force-regulating configuration. In some embodiments, drive assembly 80 may be configured to regulate the pressure applied to tissue grasped between jaw members 110, 120 to within a range of about 3 kg/cm$^2$ to about 16 kg/cm$^2$, although other pressures or pressure ranges are also contemplated.

Jaw members 110, 120 may be moved back to the open position by releasing or returning handles 30a, 30b to the spaced-apart position relative to one another and housing 20 such that drive block 84, spring 88, and drive collar 86 moves proximally. As drive collar 86 is moved proximally, drive bar 82 is pulled through shaft 12 in the proximal direction such that drive pin 105 urges jaw members 110, 120 to pivot away from one another to the open position (see FIG. 2A).

Figure 3A:
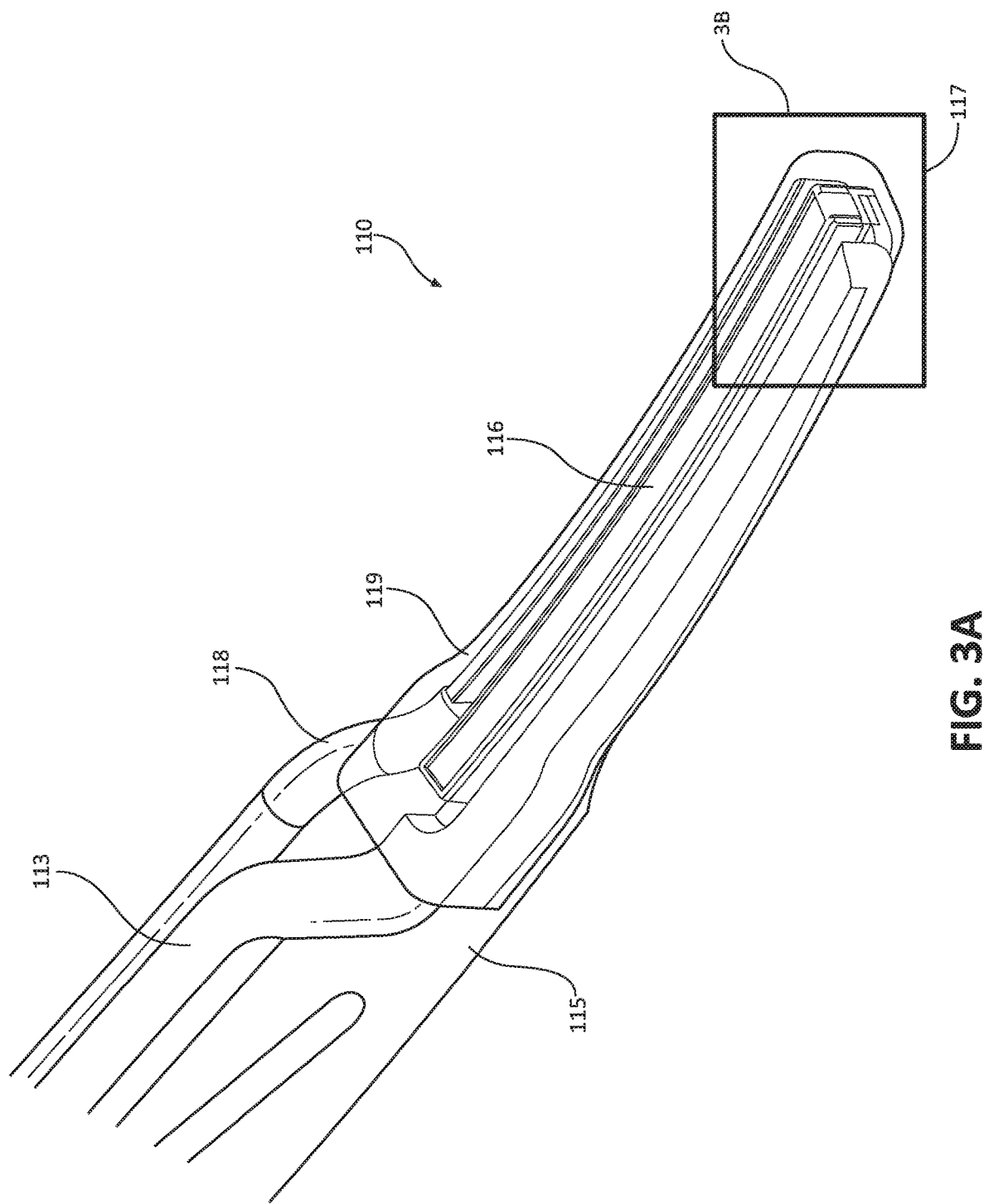
FIG. 3A is a side, perspective view of one of the jaw members of the end effector assembly of the surgical forceps of FIG. 1.
Figure 3B:
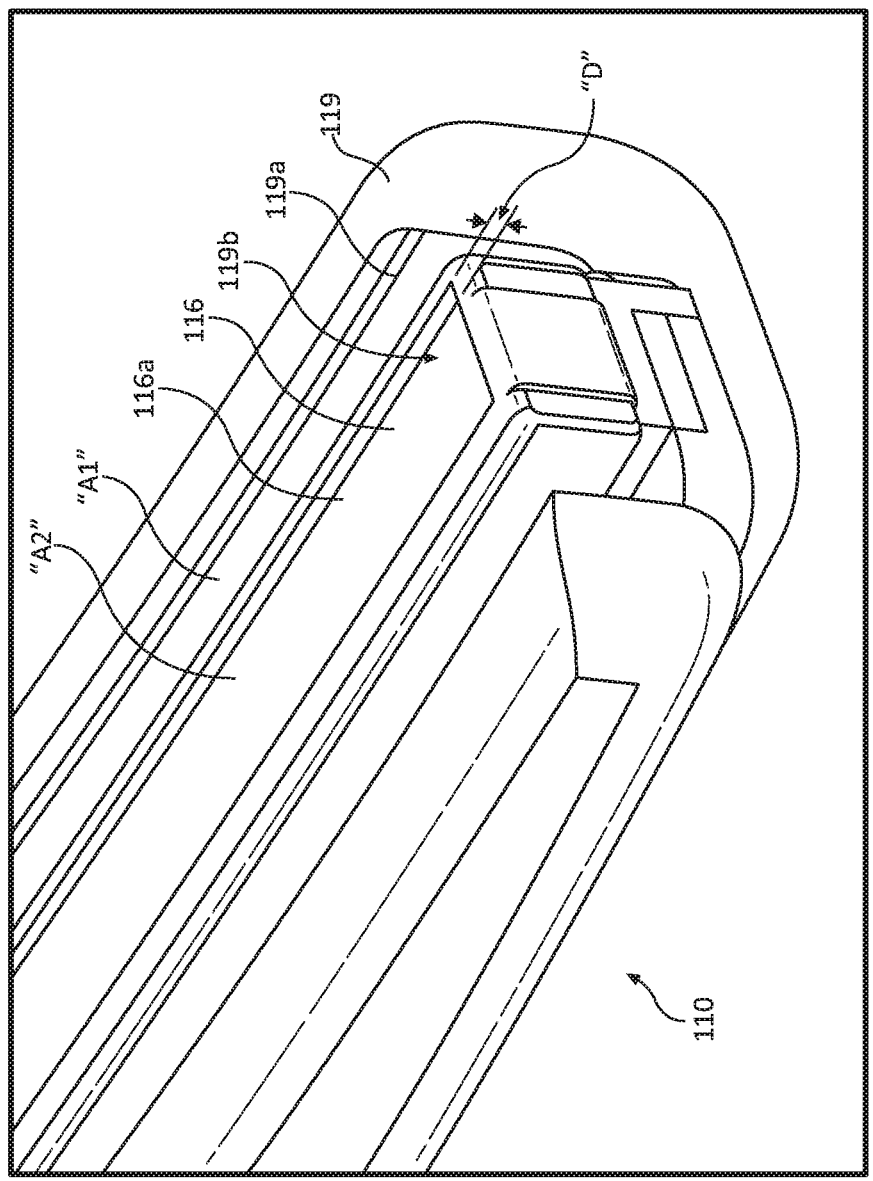
FIG. 3B is a side, perspective view of the area of detail in FIG. 3A referenced as "3B"

Turning now to FIGS. 3A and 3B, jaw member 110 of end effector assembly 100 is described in greater detail. Although only jaw member 110 is shown and described hereinbelow, it is understood that jaw member 120 defines a similar configuration.

Figure 4A:
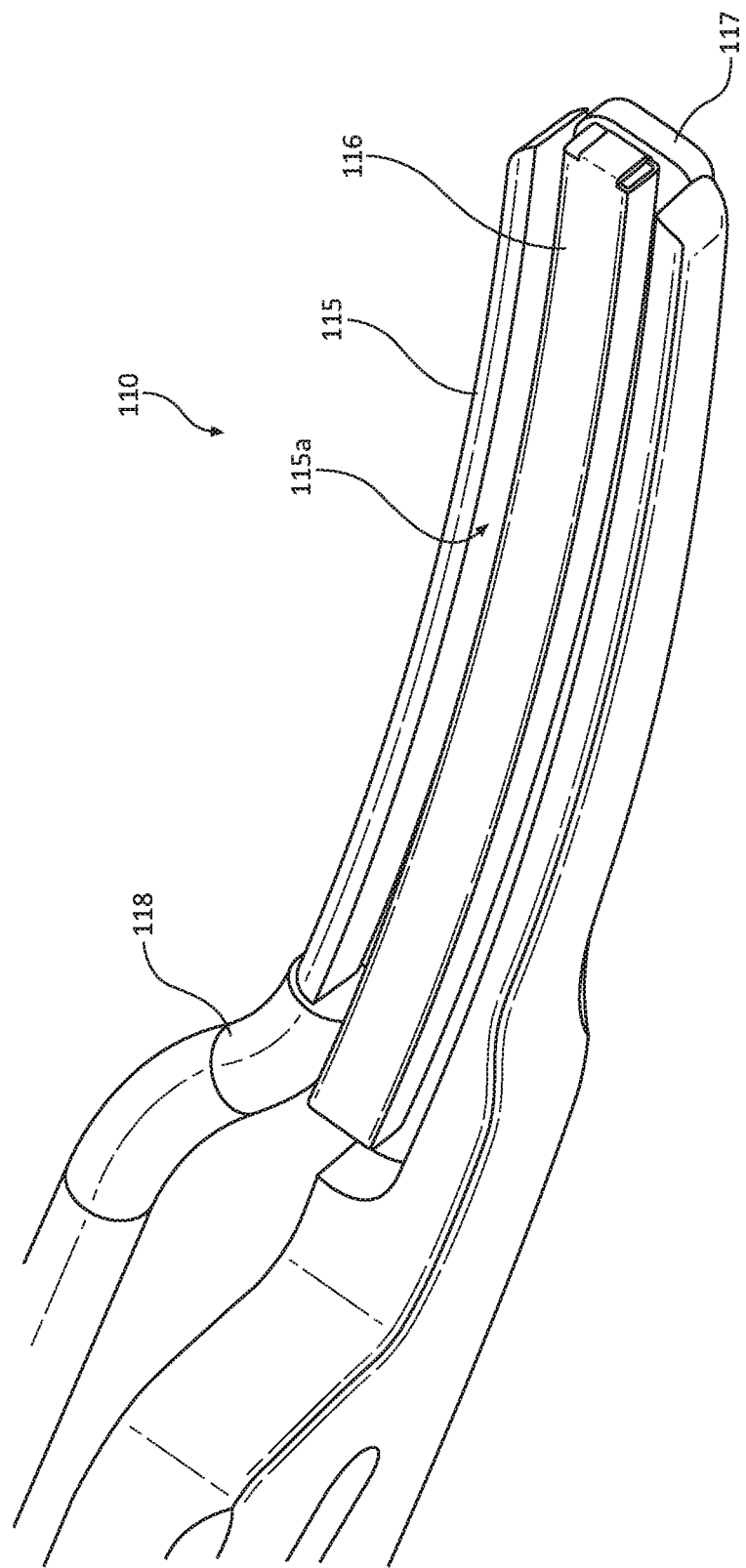
FIG. 4A is a side, perspective view of the jaw member of FIG. 3A, with the outer insulative housing removed.

Jaw member 110 includes proximal flange 113 and a jaw frame 115 extending distally from proximal flange 113. Jaw frame 115 includes a channel 115a (FIG. 4A) configured to receive an electrically-conductive plate 116 disposed over an insulative member 117 (FIG. 4A). Electrically-conductive plate 116 is electrically coupled to activation assembly 40 and the source of energy (not shown), e.g., via wire 118, which extends from jaw member 110 through shaft 12, such that energy may be selectively supplied to electrically-conductive plate 116 and conducted through tissue grasped between jaw members 110, 120 to treat tissue. The electrically-conductive plate 116, insulative member 117, and distal portion of wire 118 are encapsulated and retained in position within jaw frame 115 by an outer insulative housing 119. Outer insulative housing 119 is overmolded onto jaw frame 115, although other manufacturing processes are also contemplated. More specifically, outer insulative housing 119 surrounds jaw frame 115 and fills the portion of channel 115a not occupied by electrically-conductive plate 116 and insulative member 117.

With specific reference to FIG. 3B, outer insulative housing 119 includes a tissue contacting surface 119a and an opening 119b formed therein, within which electrically-conductive plate 116 is recessed. Opening 119b extends longitudinally through tissue contacting surface 119a and provides access to electrically-conductive plate 116 when outer insulative housing 119 is formed on, e.g., overmolded onto, jaw frame 115.

A portion of electrically-conductive plate 116 is exposed within opening 119b such that tissue contacting surface 119a of outer insulative housing 119 is raised above a tissue contacting surface 116a of electrically-conductive plate 116 a distance "D". The raised tissue contacting surface 119a of outer insulative housing 119 relative to electrically-conductive plate 116 provides a gap between electrically-conductive plate 116 of jaw member 110 and the electrically-conductive plate of jaw member 120 (not shown; which may similarly be recessed relative to an outer insulative housing of jaw member 120), thereby establishing an appropriate gap distance between the electrically-conductive plates when jaw members 110, 120 to facilitate treating tissue grasped therebetween when jaw members 110, 120 are in the closed position. End effector assembly 100 may be configured such that the gap distance (equal to twice the distance "D", where both electrically-conductive surfaces are recessed, or equal to distance "D" when only electrically-conductive surface 116a of jaw member 110 is recessed) is within a range of about 0.001 inches to about 0.006 inches, although other gap distances or gap distance ranges are also contemplated.

As shown in FIGS. 3A and 3B, an area "A1" of the raised tissue contacting surface 119a of outer insulative housing 119, which serves as the gap-setting structure of end effector assembly 100, is within an order of magnitude of, or greater than, an area "A2" of the tissue contacting surface 116a of electrically-conductive plate 116. This relatively-large area "A1" greatly reduces the stresses placed on tissue contacting surface 119a of outer insulative housing 119 at any one point when jaw members 110, 120 are closed, thereby reducing the wear and tear of tissue contacting surface 119a. As such, the need to form outer insulative housing 119 out of more-robust, thicker, or reinforced materials is obviated, thus reducing manufacturing costs associated with outer insulative housing 119.

Figure 4B:
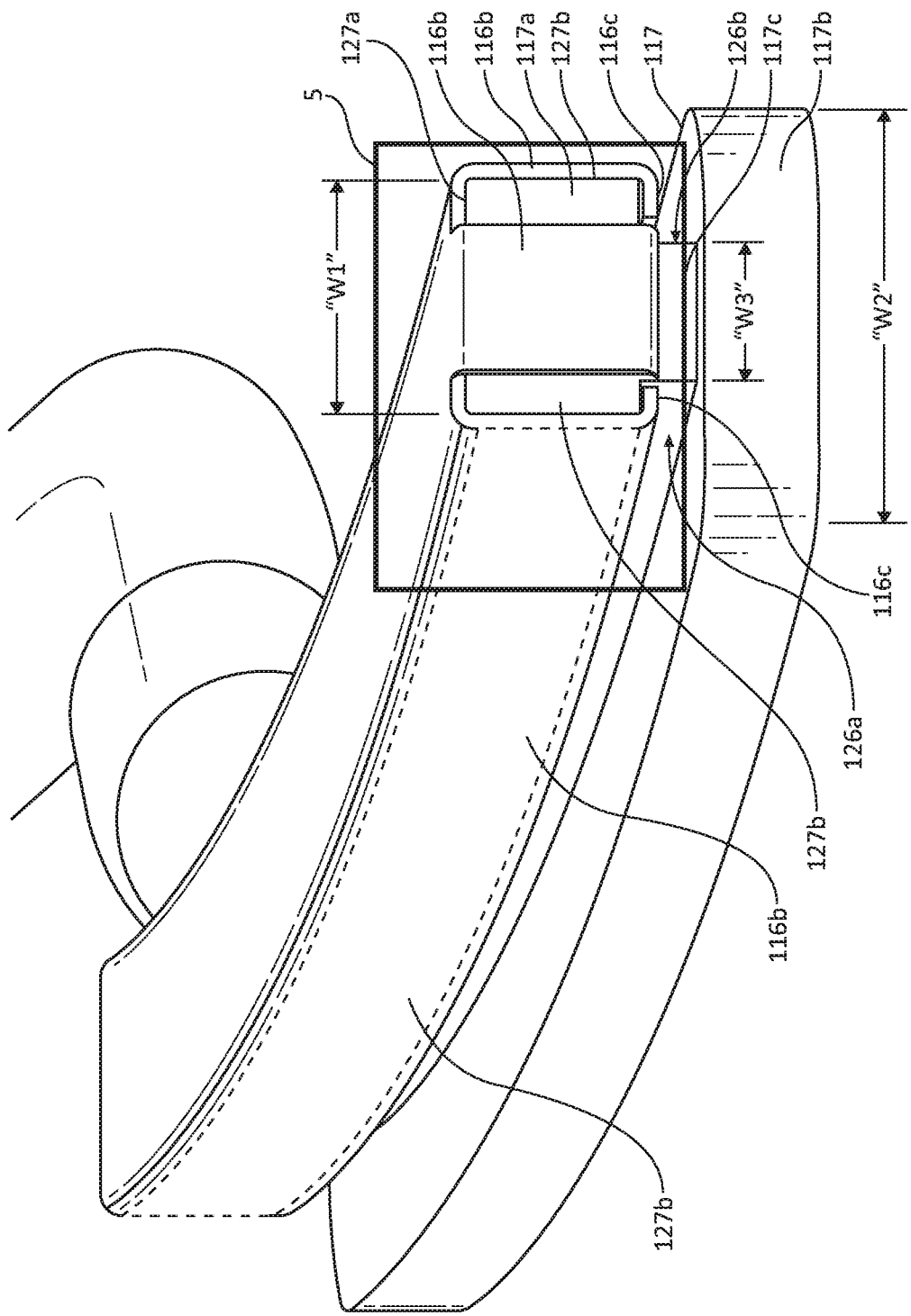
FIG. 4B is a front, perspective view of the electrically-conductive plate and insulative member of the jaw member of FIG. 3A.

With reference to FIGS. 4A and 4B, electrically-conductive plate 116 is shown disposed on insulative member 117 with outer insulative housing 119 removed (see FIG. 4A) and with jaw frame 115 removed (see FIG. 4B).

Insulative member 117 includes a substantially "I-shaped" cross-section and extends substantially along a length of channel 115a of jaw frame 115. Insulative member 117 includes a top portion 117a and a base portion 117b, where top portion 117a has a width "W1" smaller than a width "W2" of base portion 117b. Insulative member 117 also includes a body portion 117c extending between top portion 117a and base portion 117b. Body portion 117c includes a width "W3" that is less than width "W1" of top portion 117a and less than width "W2" of base portion 117b, thus defining the "I-shaped" cross-section of insulative member 117. Body portion 117c extends along the length of insulative member 117 and spaces apart top portion 117a and base portion 117b. Since width "W3" of body portion 117c is less than both, width "W1" of top portion 117a and width "W2" of base portion 117b, a pair of longitudinal grooves 126a, 126b are defined between top portion 117a and base portion 117b on opposite sides of body portion 117c.

Electrically-conductive plate 116 includes tissue contacting surface 116a disposed on a top, e.g., tissue facing surface 127a, of top portion 117a of insulative member 117 and a plurality of side portions 116b. Electrically-conductive plate 116 may be manufactured through a metal working method, such as, for example, progressive stamping. Once the flat material for electrically-conductive plate 116 is punched out, the plurality of side portions 116b are folded over a plurality of sides 127b of top portion 117a of insulative member 117, on at least three sides thereof, to correspond to the configuration of top portion 117a of insulative member 117. In embodiments, a bottom edge 116c of each of the plurality of side portions 116b may be further folded or crimped into longitudinal grooves 126a, 126b to secure electrically-conductive plate 116 onto top portion 117a of insulative member 117. In alternative embodiments, the plurality of side portions 116b of electrically-conductive plate 116 may be pressed or pierced into the plurality of sides 127b of insulative member 117. As an alternative to folding a flat piece of material to define the folds of electrically-conductive plate 116, electrically-conductive plate 116 may be formed to include the folds, such as by drawing. Thus, the term "fold" or "folded" as utilized herein is not limited to a flat (or otherwise formed) piece of material that has been folded, but also includes a material formed to include the fold(s) during formation thereof.

With additional reference to FIG. 5, electrically-conductive plate 116 is shown with insulative member 117 removed. In accordance with the present disclosure, electrically-conductive plate 116 is configured to include a reduced thermal mass "TM" to facilitate the cool down process of electrically-conductive plate 116 after supplying energy to tissue as well as the heating of electrically-conductive plate 116 upon supplying energy thereto. As can be appreciated, a low thermal mass "TM" of electrically-conductive plate 116 may also be beneficial to prevent unintended thermal spread of heat to surrounding tissue from heat retained within jaw members 110, 120 during and after treating target tissue.

The reduction in thermal mass "TM" of electrically-conductive plate 116 is accomplished by reducing a thickness "T" and a width "W4" of electrically-conductive plate 116 by an order of magnitude as compared to typical electrosurgical forceps. For example, electrically-conductive plate 116 may include width "W4" of about 0.020 inches to about 0.080 inches. Further, electrically-conductive plate 116 may include thickness "T" of about 0.001 inches to about 0.004 inches. It is contemplated that further reductions in thermal mass "TM" of electrically-conductive plate 116 may be achieved by reducing the overall length of jaw members 110, 120, and in turn electrically-conductive plate 116. Since the volume of materials used in electrically-conductive plate 116 is reduced, typically cost-prohibitive materials with higher thermal conductivity, such as, for example, gold, silver, brass, copper, and the like, may be economically used in the construction of jaw member 110.

Although not shown in the figures, the various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) may remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. For example, in embodiments, it is contemplated that electrically-conductive plate 116 may be a printed circuit board. Further, in some embodiments, electrically-conductive plate 116 may be electro-plated or electrolessly plated onto insulative member 117. In other embodiments, it is contemplated that vapor deposition may be used to deposit electrically-conductive plate 116 onto insulative member 117. Regardless of the particular materials and/or formation, the electrically-conductive plate 116 is otherwise similar to and may include any of the features detailed hereinabove. Therefore, the above description should not be construed as limiting, but merely as exemplifications of particular embodiments. Those skilled in the art will envision other modifications within the scope and spirit of the claims appended hereto.

What is claimed is:

1. A surgical forceps, comprising:
an end effector assembly including:
first and second jaw members, at least one of the first or second jaw members movable relative to the other between first and second positions, at least one of the first or second jaw members including:
a jaw frame defining a channel therein;
an insulative member disposed within the channel of the jaw frame, the insulative member including a top portion having a tissue facing surface, a bottom surface facing away from the tissue facing surface and a distal-facing portion; and
an electrically-conductive plate having a tissue contacting surface and at least one folded side portion, wherein the tissue contacting surface is disposed on the tissue facing surface of the insulative member and wherein the at least one folded side portion is folded over the top portion of the insulative member such that the electrically-conductive plate conforms to a shape of the top portion of the insulative member, wherein the at least one folded side portion is folded around the distal-facing portion of the insulative member to contact the bottom surface of the insulative member.

2. The surgical forceps according to claim 1, wherein the insulative member further includes a base portion and a body portion extending between the top portion and the base portion, wherein at least one longitudinal groove is defined between the top portion and the base portion.

3. The surgical forceps according to claim 2, wherein at least one second folded side portion of the electrically-conductive plate includes a bottom edge disposed within the at least one longitudinal groove of the insulative member.

4. The surgical forceps according to claim 1, further comprising:
an outer insulative housing formed about the jaw frame and including an opening extending therethrough, wherein at least a portion of the tissue contacting surface of the electrically-conductive plate is accessible through the opening of the outer insulative housing.

5. The surgical forceps according to claim 4, wherein the outer insulative housing defines a tissue contacting surface, the tissue contacting surface of the outer insulative housing being raised above the tissue contacting surface of the electrically-conductive plate.

6. The surgical forceps according to claim 1, wherein the top portion of the insulative member defines a first width and a base portion of the insulative member defines a second width greater than the first width.

7. The surgical forceps according to claim 6, wherein the tissue contacting surface of the electrically-conductive plate defines a third width which is between about 0.020 inches and about 0.080 inches.

8. The surgical forceps according to claim 1, wherein the electrically-conductive plate defines a thickness of about 0.001 inches to about 0.004 inches.

9. A surgical forceps, comprising:
an end effector assembly including:
first and second jaw members, at least one of the first or second jaw members movable relative to the other between first and second positions, at least one of the first or second jaw members including:
a jaw frame defining a channel therein;
an insulative member disposed within the channel of the jaw frame, the insulative member having a top portion, a base portion coupled to the top portion, a distal-facing portion, and at least one longitudinal groove defined therebetween;
an electrically-conductive plate having a tissue contacting surface and at least one folded side portion, wherein the electrically-conductive plate is disposed on the top portion of the insulative member and folded about the insulative member such that the at least one folded side portion is folded into the at least one longitudinal groove, and wherein a second folded side portion is folded around the distal-facing portion of the insulative member to contact the bottom surface of the insulative member; and
an outer insulative housing enclosing the jaw frame, the outer insulative housing including a tissue contacting surface defining an opening, wherein at least a portion of the electrically-conductive plate is accessible through the opening of the outer insulative housing to treat tissue.

10. The surgical forceps according to claim 9, wherein the tissue contacting surface of the electrically-conductive plate is recessed relative to the tissue contacting surface of the outer insulative housing.

11. The surgical forceps according to claim 9, wherein the tissue contacting surface of the electrically-conductive plate includes a first area and the tissue contacting surface of the outer insulative housing includes a second area, wherein the second area is larger than the first area.

12. The surgical forceps according to claim 9, wherein the top portion of the insulative member defines a first width and the base portion of the insulative member defines a second width greater than the first width.

13. The surgical forceps according to claim 9, wherein the tissue contacting surface of the electrically-conductive plate defines a fourth width which is between about 0.020 inches and about 0.080 inches.

14. The surgical forceps according to claim 9, wherein the electrically-conductive plate defines a thickness of about 0.001 inches to about 0.004 inches.

15. The surgical forceps according to claim 9, wherein the at least one folded side portion of the electrically-conductive plate includes a bottom edge, wherein the bottom edge is folded within the at least one longitudinal groove of the insulative member.

16. The surgical forceps according to claim 12, wherein the insulative member further includes a body portion extending between the top portion and the base portion, wherein the body portion defines a third width less than the first width of the top portion and the second width of the base portion, such that the at least one longitudinal groove is formed between the top portion and the base portion.

17. A surgical forceps, comprising:
a housing;
a shaft supported by the housing, the shaft having a distal end portion and a proximal end portion;
an end effector assembly supported at the distal end portion of the shaft, the end effector assembly including:
first and second jaw members, at least one of the first or second jaw members movable relative to the other between first and second positions, at least one of the first or second jaw members including:
a jaw frame defining a channel therein;
an insulative member disposed within the channel of the jaw frame, the insulative member including a top portion having a tissue facing surface, a bottom surface facing away from the tissue facing surface and a distal-facing portion; and an electrically-conductive plate having a tissue contacting surface and at least one folded side portion, wherein the tissue contacting surface is disposed on the tissue facing surface of the insulative member and wherein the at least one folded side portion is folded over the top portion of the insulative member such that the electrically-conductive plate conforms to a shape of the top portion of the insulative member, wherein the at least one folded side portion is folded around the distal-facing portion of the insulative member to contact the bottom surface of the insulative member; and a drive assembly disposed within the housing, the drive assembly configured to impart movement of the at least one of the first or second jaw members between the first and second positions.

\* \* \* \* \*